United States Patent [19]
Weaver

[11] Patent Number: 6,062,092
[45] Date of Patent: May 16, 2000

[54] SYSTEM FOR EXTRACTING SAMPLES FROM A STREAM

[75] Inventor: Christopher Weaver, Sacramento, Calif.

[73] Assignee: Engine, Fuel, and Emissions Engineering, Incorporated, Sacramento, Calif.

[21] Appl. No.: 09/150,632

[22] Filed: Sep. 9, 1998

[51] Int. Cl.[7] .................................................. G01N 1/00
[52] U.S. Cl. .......................................................... 73/863.03
[58] Field of Search ............................. 73/863.03, 23.31, 73/863.51, 863.834, 864.34, 864.81

[56] References Cited

U.S. PATENT DOCUMENTS

| | | |
|---|---|---|
| 3,793,887 | 2/1974 | Anderson et al. .................. 73/863.03 |
| 4,586,367 | 5/1986 | Lewis . |
| 4,633,706 | 1/1987 | Ito et al. . |
| 4,654,058 | 3/1987 | Schober et al. . |
| 4,747,297 | 5/1988 | Okayama et al. . |
| 5,033,318 | 7/1991 | Wendt .................................. 73/863.03 |
| 5,052,425 | 10/1991 | Hohenberg et al. .................. 73/863.03 |
| 5,058,440 | 10/1991 | Graze et al. . |
| 5,090,253 | 2/1992 | Kolpak . |
| 5,090,258 | 2/1992 | Yamasaki et al. .................. 73/863.03 |
| 5,101,670 | 4/1992 | Steger et al. . |
| 5,184,501 | 2/1993 | Lewis et al. . |
| 5,218,857 | 6/1993 | Decker et al. . |
| 5,333,511 | 8/1994 | Boynm et al. . |
| 5,337,595 | 8/1994 | Lewis . |
| 5,410,907 | 5/1995 | Ström et al. . |
| 5,469,731 | 11/1995 | Decker et al. ...................... 73/863.03 |

FOREIGN PATENT DOCUMENTS 0039189  3/1979  Japan .................................. 73/863.03

OTHER PUBLICATIONS

The Measurement of Gaseous and Particulate Emissions from Light–Duty and Heavy–Duty Motor Vehicles Under Road Driving Conditions, Potter et al, undated.
Method 5—Determination of Particulate Emissions from Stationary Sources, U.S. E.P.A., Sep. 25, 1989.

*Primary Examiner*—Robert Raevis
*Attorney, Agent, or Firm*—Theodore J. Bielen, Jr.

[57] ABSTRACT

A system for extracting samples from a stream in a conduit utilizing a probe, placed in the stream and having a channel for passing samples from the conduit stream. First and second pressure taps measure the pressure inside and outside the probe. A feedback signal, based on a pressure differential relative to the probe, is generated and controls a valve regulating sample velocity flow through the probe channel, that bears a fixed proportion to the velocity of flow in the conduit. The constant of proportionality between flow velocities in the conduit and the probe may be 1.0, resulting in an isokinetic sampling condition.

9 Claims, 3 Drawing Sheets

SYSTEM FOR EXTRACTING SAMPLES FROM A STREAM

BACKGROUND OF THE INVENTION

The present invention relates to a system for extracting samples from a stream flowing in a conduit, which is portable and operates on either an isokinetic or a constant volume sampling basis.

Constant volume sampling (CVS) has been recognized as the most accurate way of measuring pollutant emissions under conditions of varying flow rate, for example, exhaust emissions of a vehicle driven at varying speeds. In a CVS system, the exhaust stream containing the pollutants is diluted with clean air such that the combined flow rate of the mixture of exhaust gases and clean air is substantially constant. As a result, the pollutant concentration in the diluted mixture is proportional to the mass flow rate of pollutants in the exhaust stream. Moreover, particulate components are condensed and measured. However, such CVS sampling systems in existence are relatively large and expensive. As a practicality, these systems do not accurately measure exhaust streams from large engines, such as those used in locomotives and heavy trucks. In addition, such systems are not portable.

Portable emission sampling systems have also been developed. However, such systems are generally not CVS systems. Instead, prior portable emissions sampling systems rely on measurements of pollutant concentration in the undiluted exhaust and are combined or compared to a direct or indirect measurement of exhaust flow rate. Unfortunately, these portable pollutant concentration systems are inaccurate, since the measuring or estimating of exhaust flow rates varies from vehicle to vehicle. In addition, present pollutant concentration measurement systems are unable to determine particulate emissions accurately.

U.S. Pat. No. 5,090,253 describes a flow meter which is used to measure fluid from an exhaust conduit.

U.S. Pat. No. 5,333,511 shows a batch exhaust analyzer which is programmed to obtain samples at certain times.

U.S. Pat. Nos. 4,586,367, 4,633,706, 4,654,058, and 4,747,297 describe apparatuses for measuring particulate matter in exhaust streams, with or without the use of dilution tubes.

U.S. Pat. Nos. 5,058,440, 5,101,670, 5,218,857, and 5,410,907 show pollutant concentration sampling devices which use dilution tunnels. U.S. Pat. Nos. 5,184,501 and 5,337,595 employ pollutant concentration type samplers which also measure bulk stream flow rates.

A paper entitled "The Measurement of Gaseous and Particulate Emissions from Light-Duty and Heavy-Duty Motor Vehicles Under Road Driving Conditions" by Potter, C. J. et al describes an emission sampling system which operates on a CVS principle. This system employs a passive cap for the end of the vehicle exhaust pipe to divide the exhaust flow among a large number of identical parallel small pipes. One of the pipes leads to a dilution tunnel. To maintain proportional flow through all of the pipes, the system requires that the pressure drop across the cap be much greater than the pressure drop between the cap and the dilution tunnel. Changing the pressure in the exhaust system affects the generation of pollutant emissions. Inaccurate measurements ensue, especially in turbocharged engines. In addition, the system is unwieldy for mounting to a vehicle.

In measuring particulate emissions from exhaust streams, such as chimney outflows having particles larger than a few microns, it is important to maintain isokinetic sampling conditions. In other words, the velocity of the gas entering a sample probe must possess substantially the same velocity as the gas in the exhaust stream. If such condition is not achieved, the inertia of particles in the exhaust stream may result in a sample being enriched or depleted in particles, relative to the concentration of particles in the exhaust stream. U.S. E.P.A. Method 5—"Determination of Particulate Emissions from Stationary Sources" documents a standard procedure for measuring particulate emissions in stationary exhaust stacks, using isokinetic sampling. The method requires the use of a separate pitot tube and orifice meter. Manual adjustments and calculations achieve isokinetic sampling only under steady state conditions.

A system which is capable of automatically extracting a proportional or isokinetic sample of gas and/or particulate emissions from an exhaust stream under varying flow rates, which is portable, accurate, and does not interfere with the exhaust stream would be a notable advance in the field of emission measurements.

SUMMARY OF THE INVENTION

In accordance with the present invention a novel and useful system for extracting samples from a stream is herein provided.

The portable emission system of the present invention utilizes a probe which may be located in the exhaust conduit of an internal combustion engine such as those found in a vehicle. The probe includes a channel for gathering and passing emissions from the exhaust conduit for analysis. The probe may take the form of a tube which extends a certain distance into the exhaust conduit with its long axis parallel to the direction of flow of emissions or constituents in the exhaust conduit. The probe is intended to extract a fixed proportion of the total exhaust gas flow, i.e. isokinetic sampling conditions.

To maintain constant volume and isokinetic conditions at the probe inlet within the exhaust conduit, means is employed for controlling the velocity of flow through the probe channel to correspond to the velocity of flow through the exhaust conduit. To achieve this result, means is provided for generating a feedback signal representing the relative velocities of flow through the exhaust conduit and flow through the probe channel. In this regard, first pressure measuring means determines the pressure within the probe channel and second pressure measuring means determines the pressure in the exhaust conduit. Both pressure measurements are sent to comparator means where the pressure differential is transduced into an electrical signal representing such pressure differential.

The present CVS system also includes a dilution conduit carrying ambient air, or other diluent fluid, from a source by the use of a blower or pump. Ambient air, or other diluent fluid, from the source is also filtered in this regard. The probe channel delivers emissions through an exhaust line to the dilution conduit at a place of entry downstream from the ambient air source. Valve means is provided in the dilution conduit to regulate the flow rate of ambient air. The valve means utilizes the signal from the comparator means and provides throttling of the flow of ambient air in response to the same. In other words, to increase the flow rate of emissions from the probe channel, the flow of ambient air through the dilution tube is reduced and vice versa. In any case, the velocity of the sample flowing through the probe channel and the velocity of constituents flowing through the exhaust conduit are maintained correspondent to one another, i.e., essentially equal.

A sample is tapped from the dilution tunnel downstream of the place of entry of the emissions exhaust line from the probe channel. Such sample tap is then sent to an instrument which continuously measures the concentration of emissions, or to a batch type measuring device. The latter is particularly useful in measuring particulate emissions from an internal combustion engine. Both the batch and continuous measurement determine emission concentrations proportional to the mass flow of emissions in the vehicle exhaust conduit. A background sample may also be taken upstream of the place of entry of the emissions exhaust line.

In an isokinetic version of the system of the present invention, the feedback signal regulates a pump which forces exhaust particulates into a filter. Particulate-free gas is then sent to a condenser and gas meter. Measurements of the metered gas, condensate, and filter particulates determines particulate concentration.

It may be apparent that a novel and useful system for sampling emissions from an exhaust conduit has been described.

It is therefore an object of the present invention to provide a system for sampling emissions from an exhaust conduit of a pollution source which extracts particulate samples on an isokinetic basis.

Another object of the present invention is to provide a system for sampling emissions from an internal engine by which a probe in an exhaust conduit of the internal combustion engine extracts a fixed proportion of the total exhaust gas flow.

A further object of the present invention is to provide a system for sampling emissions from an exhaust conduit of an internal combustion engine which may be used to measure such emissions as a fraction of the total exhaust flow without changing the exhaust back pressure or otherwise affecting the operation of the internal combustion engine.

Yet another object of the present invention is to provide a system for sampling emissions from an exhaust conduit of an internal combustion engine which is capable of measuring gaseous pollutants and particulate matter pollutants.

A further object of the present invention is to provide a system for sampling components in a conduit stream which is portable and does not require extensive adaption to engines of various sizes.

Another object of the present invention is to provide a system for sampling emissions from an exhaust conduit of an internal combustion engine which is accurate and does not require the independent measurement of the exhaust mass flow rate from the exhaust conduit of the internal combustion engine.

Another object of the present invention is to provide a system for sampling emissions from an exhaust conduit of an internal combustion engine which is capable of determining measurements of particulate matter in the exhaust conduit and provides necessary cooling without additional equipment required in the prior art.

Another object of the present invention is to provide a system which is capable of measuring pollutant emissions from motor vehicles on a portable constant volume sampling basis, and is capable of measuring particulate emissions from chimneys on an isokinetic sampling basis.

A further object of the present invention is to provide a system for extracting and diluting a continuous proportional sample of the exhaust flow from a source that obviates the need for using a special cap on the exhaust conduit, which creates a detrimental backpressure on the exhaust conduit.

The invention possesses other objects and advantages especially as concerns particular characteristics and features thereof which will become apparent as the specification continues.

For a better understanding of the invention references made to the following detailed description of the preferred embodiments which should be taken in conjunction with the hereinabove described drawings.

DETAILED DESCRIPTION OF THE PREFERRED EMBODIMENTS

Various aspects of the present invention will evolve from the following detailed description of the preferred embodiments thereof, which should be referenced to the previously described drawings.

Figure 1:
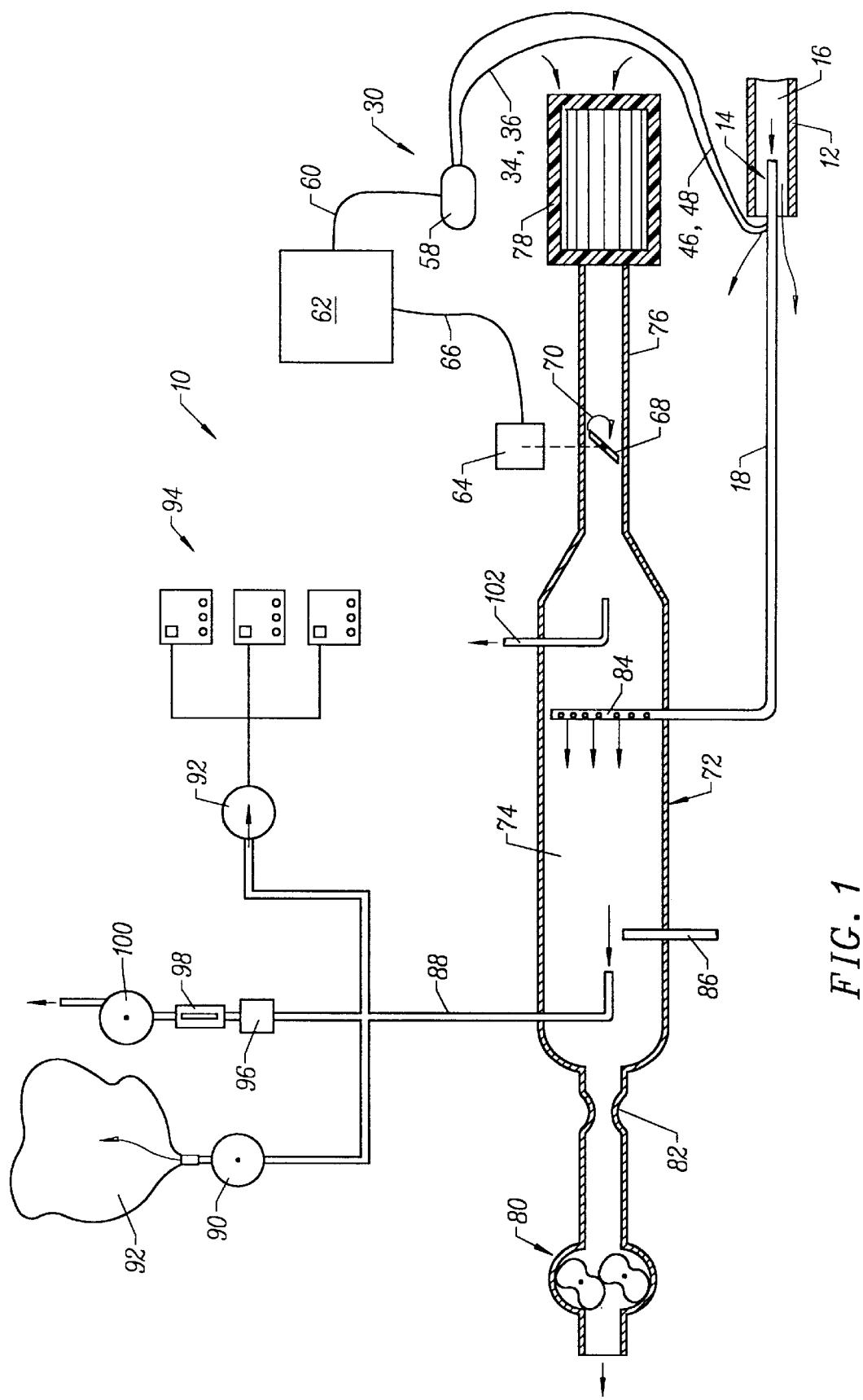
FIG. 1 is a flow diagram of the system of the present invention demonstrating constant volume sampling.

The invention as a whole is shown in the drawings by reference character 10, FIG. 1. Generally system 10 may be used to extract samples from a stream flowing in a conduit. In the present embodiment, system 10 is employed to obtain accurate emission samples from exhaust conduit 12 which may lead from any internal combustion engine such as that found in an automobile, truck, train, boat, and the like. Typically, the emissions measured from exhaust conduit 12 include oxides of nitrogen (NOx), carbon monoxide (CO), carbon dioxide ($CO_2$), and particulate matter such as unburned hydrocarbons. System 10 of the present invention is deemed to be a portable type system, one that can be mounted on and "ride along" with the vehicle to measure emissions while such vehicles are operating in a normal fashion. The present system obviates the need for an expensive chassis dynamometer system of the prior art. Also, the system 10 of the present invention is responsive to rapid changes in exhaust flow rates which are the result of differences in engine speed.

Figure 2:
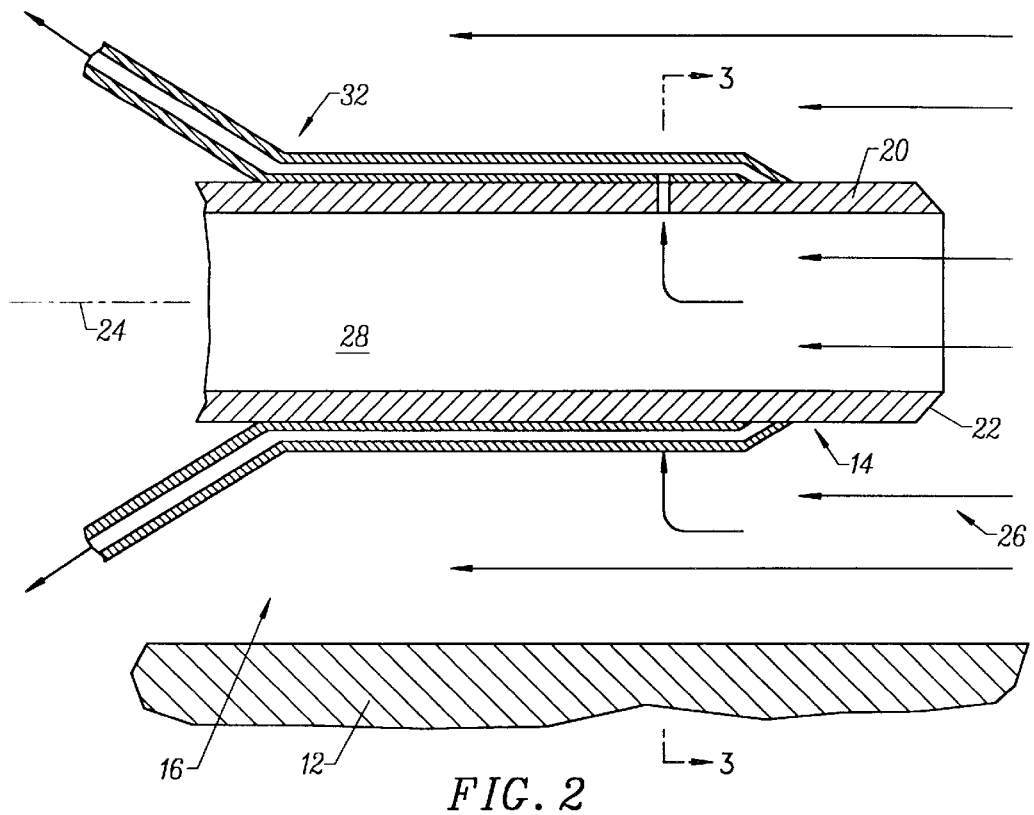
FIG. 2 is a sectional view of the probe of the present invention.

System 10 includes as one of its elements a probe 14 which is located within chamber 16 of exhaust conduit 12. Probe 14 directly connects to an exhaust line or channel 18 which passes exhaust gas from exhaust chamber 16 of conduit 12. Referring now to FIG. 2, it may be observed that probe 14 is in the form of a tube 20 having a mitred edge 22. The long axis 24 of probe 14 is positioned essentially parallel to the directional flow of gases through exhaust conduit 12, represented by multiplicity of directional arrows 26. The probe 14 is held in that position by any suitable fastening means such as a bracket (not shown). Thus, a portion of the exhaust gas from the engine associated with exhaust conduit 12 flows through chamber 28 of probe 14.

Figure 3:
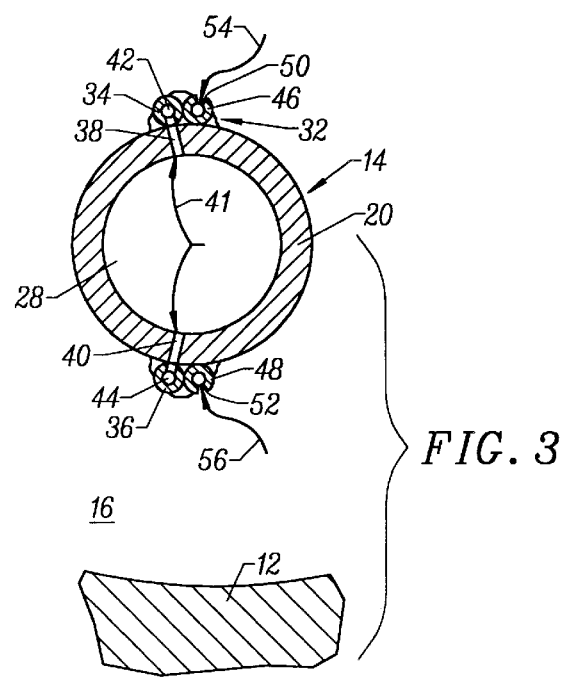
FIG. 3 is a sectional view taken along line 3—3 of FIG. 2.

Means 30 is also provided for controlling the velocity of the exhaust gas stream through chamber 28 of probe 14. Again, referring to FIG. 2, means 30 utilizes a quartet of tubes 32 which are mounted to the exterior of probe tube 22 by any suitable means such as high-temperature vacuum brazing. For example, probe tube 20 may possess a central diameter of approximately 8 mm while each of the plurality of tubes 32 might possess a diameter of approximately 2 mm. Referring to FIG. 3, it may be observed that tubes 34 and 36 include static pressure taps or openings 38 and 40, respectively, to chamber 28 of tube 20. Directional arrows 41 indicate that chambers 42 and 44 of tubes 34 and 36 communicate with chamber 28 of tube 20. Tubes 46 and 48, on the other hand, include pressure taps 50 and 52 which communicate with chamber 16 of exhaust conduit 12. Directional arrows 54 and 56 indicate this communication. Thus, tubes 34 and 36 are capable of measuring the static pressure within chamber 28 of probe tube 20, while tubes 46 and 48 are capable of measuring the static pressure within exhaust conduit 12. Dual tubes are employed to eliminate disparate measurements of probe 12, due to the effect of small misalignments between the long axis 24 of probe 14 and the direction of flow, directional arrows 26, of the exhaust gas in exhaust conduit 12.

Turning again to FIG. 1, pairs of tubes 34 and 36 and pairs of tubes 46 and 48, each pair combined to a single tube, pass to differential pressure sensor or comparator 58. Sensor 58 produces an electrical signal which is sent through electrical leg 60 to automatic controller 62. An electrical feedback signal is then sent to stepping motor 64 via electrical conduits 66. Stepping motor 64 is capable of rotating throttle valve 68 according to directional arrow 70, the purpose of which will be discussed hereinafter.

System 10 further includes a dilution conduit or tunnel 72, FIG. 1, which is of sufficient length and provides sufficient flow to assure turbulent mixing within chamber 74 of the same. Channel 18 communicates with dilution conduit 72. Neck 76 of dilution conduit connects to a filter 78. Ambient air, or other diluent fluid, from a source (usually the external atmosphere) flows through filter 78 by the motivating power of pump 80, which may be a blower. Blower 80 is used in conjunction with a critical flow venturi 82. Thus, throttle 68 is rotated by stepping motor 64 to control the flow of air through dilution tunnel 72. Differential pressure sensor 58 may detect a static pressure inside probe chamber 28 which is higher than the static pressure within chamber 16 of exhaust conduit 12. In such a case, throttle 68 will close slightly. The terminus 84 of exhaust line 18, located downstream of ambient air filter 78, senses a slight decrease in pressure. This causes the rate of flow through the exhaust line 18 to increase. This, in turn, increases the velocity of exhaust gases within chamber 28 of tube 20 and lowers the pressure differential between chamber 28 of tube 20 and chamber 16 of exhaust conduit 12. Conversely, throttle 68 will open slightly when a higher pressure is detected in chamber 16 of conduit 12 than in chamber 28 of tube 20. This, in turn, reduces the flow of exhaust sample through exhaust line 18. Thus, a proportional sampling condition exists between tube 20 and exhaust conduit 12 due to the zeroing-out of the pressure differential between chambers 28 and 16, respectively. It should be noted that temperature sensor 86 may be employed in certain cases within chamber 74 of dilution conduit 72.

The sample tap 88 within chamber 74 downstream of terminus 84 of exhaust sample line 18 directs a properly diluted sample of constituents therein, such as gaseous and particulate pollutants, for analysis. For example, pump 90 and sample bag 92 are capable of gathering gaseous pollutants in a batch process for analysis. On the other hand, pump 90 and continuous gas monitor 94 are capable of analyzing pollutants on a continuous level.

Continuous gas monitor 94 may take the form of a California Analytical Instruments Model ZRH, for measuring CO and $CO_2$, and a Thermo Electron Model 42 analyzer for measuring $NO_x$. Filter 96, flow meter 98, and pump 100 continually withdraw samples, containing constituents, from sample tap 88 and send the same to the ambient atmosphere. It should be noted that filter 96 may be used to collect particulate matter in many cases. Background sample tap 102 is employed to monitor the gaseous chemicals in the ambient air upstream at exhaust line terminal 84.

Figure 4:
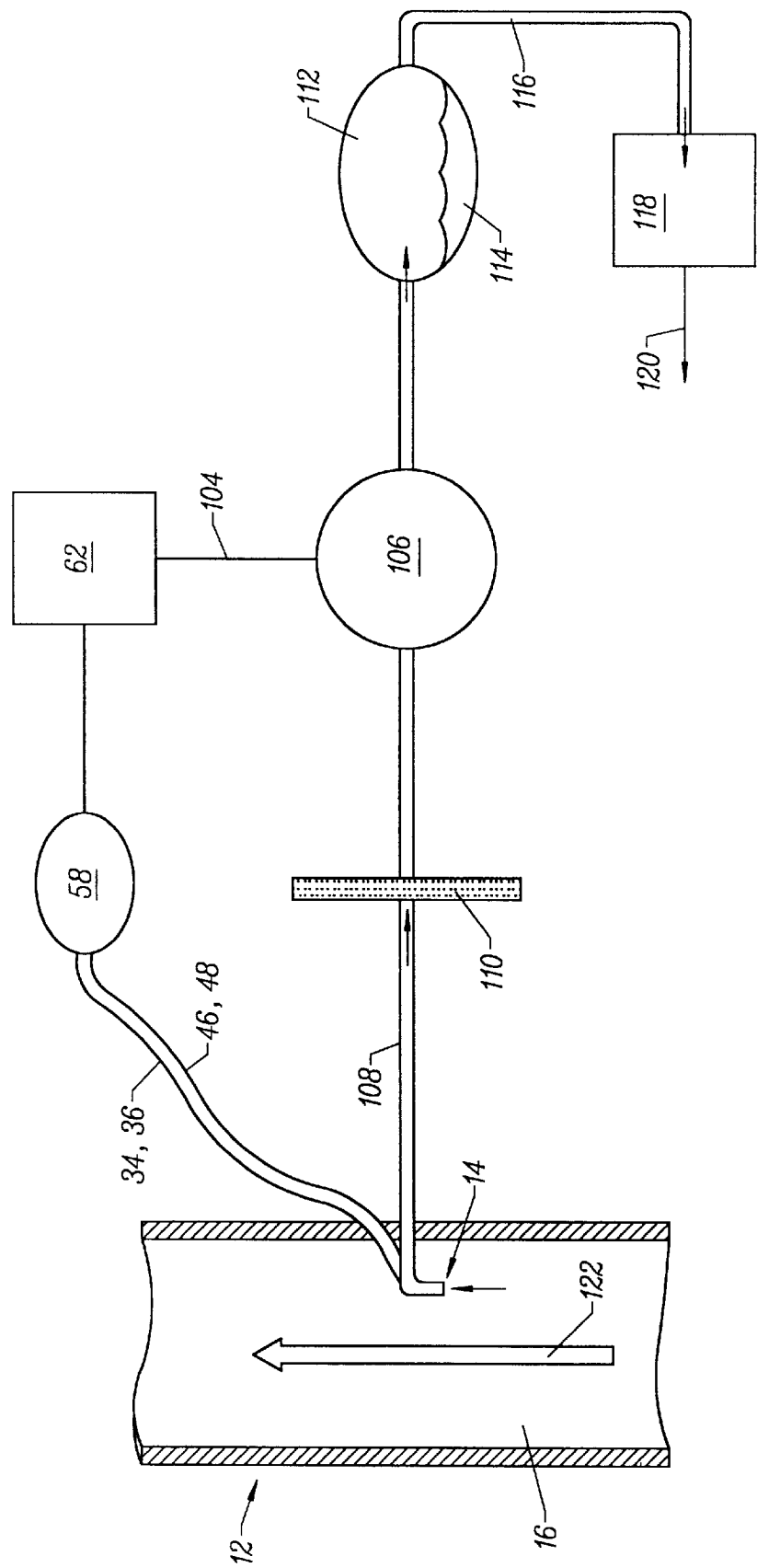
FIG. 4 is a flow diagram of the system demonstrating isokinetic sampling.

Referring now to FIG. 4, an isokinetic application of the system of the present invention is shown in which probe 14 is placed within chamber 16 of exhaust conduit 12. Pairs of tubes 34, 36 and 46, 48 lead from probe 14 in the same manner as the embodiment depicted in FIG. 1. Differential pressure sensor or comparator 58 produces an electrical signal, again, to controller 62. Electrical output leg 104 of controller 62 sends a signal to variable speed pump 106 which pulls a gas sample containing particulate matter through conduit 108 and to filter 110. Exhaust material, generally in gaseous form, then passes to condenser 112 where liquids are formed. In most cases, such liquids take the form of water body 114. Gases from condenser pass from condenser 112 through conduit 116, to dry gas meter 118. Arrow 120 represents the exhaust stream from dry gas meter 118.

In operation, FIG. 1, probe 14 is placed within exhaust gas conduit 12 in axial position. Pollutant samples pass through probe 14 and exhaust line 18, exiting the same at terminus 84 within dilution conduit 72. Means 30 for controlling the velocity through probe 14 includes pairs of tubes 34 and 36 and 46 and 48 to determine the differential pressure between chamber 16 of exhaust conduit 12 and interior chamber 28 of probe tube 20. An isokinetic condition may be maintained between probe 14 and exhaust conduit 12 by means 30. Thus, a gaseous sample exiting terminus 84 is properly diluted resulting in pollutant quantities proportional to those in exhaust conduit 12. This result is achieved by pairs of tubes 34 and 36, as well as, 46 and 48 which measure the pressure differential between probe 14 and exhaust conduit 12. Differential pressure sensor 58, controller 62, stepping motor 64, and throttle 68 adjusts the flow of ambient air through dilution tube 72. Sample tap 88 passes properly diluted emission samples to a batch analysis at sample bag 92 or to continuous sampler 94. Particulate matter may be collected for later analysis at filter 96 adjacent flow meter 98 in the pump 100. Background sample tap 102 is used to analyze the ambient air prior to the injection of the exhaust gas sample through terminus 84 of exhaust line 18 within dilution conduit 72.

Turning to FIG. 4, the isokinetic operation is illustrated in which probe 14 produces a feedback signal through electrical leg 104 in the same manner as shown in FIG. 1, via differential pressure sensor 58 and controller 62. Feedback signal 104 regulates the speed of pump 106 according to the velocity of the exhaust stream within chamber, 16 represented by directional arrow 122. Thus, particulates passing through conduit 108 and are captured by filter 110. The particulate matter found in filter 110 under such isokinetic sampling conditions represent a fixed proportion of the total particulates in the exhaust flow 122 within chamber 116 of exhaust conduit 12. In other words, filter 110 has captured or acquired a fixed fraction of the total exhaust flow 122 without changing the exhaust back pressure within conduit 12, or otherwise affecting the operation of the vehicle to which exhaust conduit 12 is connected. Weighing the particulates in filter 110, water body 114 in condenser 112, and the quantity of air detected by meter 118 results in a measurement of particulate concentration within conduit 12. Thus, the instantaneous mass emission rate is determined.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A system for extracting samples from a stream flowing in a conduit, comprising:

a. a probe located in said conduit, said probe including a channel probe passing a sample flow in the conduit for analysis;

b. regulating means for controlling the velocity of the sample flow through said probe channel to correspond to the velocity of the stream flowing in the conduit, said regulating means comprising means for generating a feedback signal representing the relative velocities of the stream flowing in the conduit and the sample flow through said probe channel, said means for generating a feedback signal further comprising first pressure measuring means for determining the pressure within said probe channel, second pressure measuring means for determining the pressure in the conduit, and comparator means for measuring the pressure differential between pressure determined by said first and second pressure measuring means and for generating a signal representative of said pressure differential;

c. a dilution conduit carrying diluent fluid from a source, said probe channel communicating with said dilution conduit at a place of entry downstream from said source of diluent fluid; and d. valve means for regulating the flow rate of diluent fluid in said dilution conduit and the flow of sample from said probe channel, according to said comparator means signal.

2. The system of claim 1 in which said valve means is located in said dilution conduit between said place of entry of said sample from said probe channel and said source of diluent fluid.

3. The system of claim 2 in which said dilution conduit further includes a pump.

4. The system of claim 3 in which said dilution conduit further includes a filter for filtering said source of diluent fluid.

5. The system of claim 4 which further comprises a sample tap extending into said dilution conduit at a place downstream of said place of entry of sample from said probe channel.

6. The system of claim 5 which additionally comprises means for continuously measuring the concentration of constituents in said sample tap.

7. The system of claim 5 in which additionally comprises means for measuring the concentration of constituents in said sample tap on a batch basis.

8. The system of claim 7 which additionally comprises means for continuously measuring the amount of constituents in said sample tap.

9. The system of claim 1 in which said means for generating a feedback signal further comprises first pressure measuring means for determining the pressure within said probe channel, second pressure measuring means for determining the pressure in the conduit, and comparator means for measuring the pressure differential between pressure determined by said first and second pressure measuring means and for generating a signal representative of said pressure differential.

* * * * *